(12) United States Patent
Argyropoulos et al.

(10) Patent No.: US 6,307,110 B1
(45) Date of Patent: Oct. 23, 2001

(54) SEPARATION PROCESSES

(75) Inventors: John Nicholas Argyropoulos, Scott Depot; Jeffrey Scott Kanel, Hurricane; Michael Leo Tulchinsky; David James Miller, both of Charleston; Donald Lee Morrison, Hurricane; Paul Foley, Barboursville; David Robert Bryant, So. Charleston; Ailene Gardner Phillips, Charleston; Brian Michael Roesch, Cross Lanes; John Robert Briggs, Charleston; Max Min Lee, Charleston; John Michael Maher, Charleston, all of WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 0 days.

(21) Appl. No.: 09/526,337

(22) Filed: Mar. 15, 2000

(51) Int. Cl.$^7$ .................................................... C07C 45/50
(52) U.S. Cl. ...................... 568/454; 568/451; 568/453; 560/177; 558/85; 556/13; 556/25
(58) Field of Search ................................. 568/451, 453, 568/454; 560/177; 558/85; 556/13, 25

(56) References Cited

U.S. PATENT DOCUMENTS

| | | |
|---|---|---|
| 3,904,547 | 9/1975 | Aycock et al. . |
| 4,300,002 | 11/1981 | Shibatani et al. . |
| 4,633,021 | 12/1986 | Hanes . |
| 4,845,306 | 7/1989 | Puckette . |
| 5,138,101 | 8/1992 | Devon . |
| 5,180,854 | 1/1993 | Abatjoglou et al. . |
| 5,264,616 | 11/1993 | Roeper et al. . |
| 5,463,082 | 10/1995 | Horvath et al. . |
| 5,648,554 | 7/1997 | Mori et al. . |
| 5,719,312 | 2/1998 | Hansen et al. . |
| 5,756,854 | 5/1998 | Bahrmann et al. . |
| 5,773,666 | 6/1998 | Omatsu et al. . |
| 5,789,625 | 8/1998 | Bryant et al. . |
| 5,847,228 | 12/1998 | Monflier et al. . |
| 5,932,772 | 8/1999 | Argyropoulos . |
| 5,952,530 | 9/1999 | Argyropoulos . |

FOREIGN PATENT DOCUMENTS

| | | |
|---|---|---|
| 0922691A1 | 6/1999 | (EP) . |
| 23850A74 | 6/1975 | (IT) . |
| 9715543 | 5/1997 | (WO) . |
| 9906345 | 2/1999 | (WO) . |

OTHER PUBLICATIONS

Article; Journal of Chemical Society of Japan 9/92, vol. 2 pp. 119–127, New Processes for 1–Octanol and Various Diols Using Noble Metal Complex Catalysts, Yoshimura, N., Y. Tokitoh, M. Matsumoto.

Article: Journal of Am. Chem. Soc. 1993, 115, 2066–2068, Practical, High–Yield Regioselective, Phodium–Catalyzed Hydroformlation of Functionalized A–Olefins, Gregory D. Cuny and Stephen L. Buchwald.

*Primary Examiner*—Paul J. Killos
(74) *Attorney, Agent, or Firm*—Warren K. Volles

(57) ABSTRACT

This invention relates to a process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products, one or more nonpolar solvents and one or more polar solvents by phase separation wherein (i) the selectivity of the nonpolar phase for the organophosphorus ligand with respect to the one or more products is expressed by a partition coefficient ratio Ef1which is a value greater than about 2.5, (ii) the selectivity of the nonpolar phase for the organophosphorus ligand with respect to the one or more organophosphorus ligand degradation products is expressed by a partition coefficient ratio Ef2 which is a value greater than about 2.5, and (iii) the selectivity of the nonpolar phase for the organophosphorus ligand with respect to the one or more reaction byproducts is expressed by a partition coefficient ratio Ef3 which is a value greater than about 2.5.

23 Claims, No Drawings

SEPARATION PROCESSES

RELATED APPLICATION

This application is related to copending U.S. patent application Ser. No. (D-17982), filed on an even date herewith, the disclosure of which is incorporated herein by reference.

BRIEF SUMMARY OF THE INVENTION

1. Technical Field

This invention relates to improved metal-organophosphorus ligand complex catalyzed processes. More particularly this invention relates to metal-organophosphorus ligand complex catalyzed processes in which the desired product, along with any organophosphorus ligand degradation products and reaction byproducts, can be selectively extracted and separated from the reaction product fluid by phase separation.

2. Background of the Invention

It is known in the art that various products may be produced by reacting one or more reactants in the presence of an metal-organophosphorus ligand complex catalyst. However, stabilization of the catalyst and organophosphorus ligand remains a primary concern of the art. Obviously catalyst stability is a key issue in the employment of any catalyst. Loss of catalyst or catalytic activity due to undesirable reactions of the highly expensive metal catalysts can be detrimental to the production of the desired product. Moreover, production costs of the product obviously increase when productivity of the catalyst decreases.

For instance, a cause of organophosphorus ligand degradation and catalyst deactivation of metal-organophosphorus ligand complex catalyzed hydroformylation processes is due in part to vaporizer conditions present during, for example, in the vaporization employed in the separation and recovery of the aldehyde product from the reaction product mixture. When using a vaporizer to facilitate separation of the aldehyde product of the process, a harsh environment of a high temperature and a low carbon monoxide partial pressure than employed during hydroformylation is created, and it has been found that when a organophosphorus promoted rhodium catalyst is placed under such vaporizer conditions, it will deactivate at an accelerated pace with time. It is further believed that this deactivation is likely caused by the formation of an inactive or less active rhodium species. Such is especially evident when the carbon monoxide partial pressure is very low or absent. It has also been observed that the rhodium becomes susceptible to precipitation under prolonged exposure to such vaporizer conditions.

For instance, it is theorized that under harsh conditions such as exist in a vaporizer, the active catalyst, which under hydroformylation conditions is believed to comprise a complex of rhodium, organophosphorus ligand, carbon monoxide and hydrogen, loses at least some of its coordinated carbon monoxide, thereby providing a route for the formation of such a catalytically inactive or less active rhodium. Accordingly, a successful method for preventing and/or lessening such degradation of the organophosphorus ligand and deactivation of the catalyst as occur under harsh separation conditions in a vaporizer would be highly desirable to the art.

Organophosphorus ligand degradation and catalyst deactivation of metal-organophosphorus ligand complex catalyzed hydroformylation processes can occur under process conditions other than vaporizer conditions. The buildup of organophosphorus ligand degradation products as well as reaction byproducts in the reaction product fluid can have a detrimental effect on the process, e.g., decreases catalyst efficiency, raw material conversion and product selectivity. Accordingly, a successful method for preventing and/or lessening such buildup of organophosphorus ligand degradation products and reaction byproducts in the reaction product fluid would be highly desirable in the art.

DISCLOSURE OF THE INVENTION

It has now been discovered that in metal-organophosphorus ligand complex catalyzed processes, the desired product, along with any organophosphorus ligand degradation products and reaction byproducts, can be selectively extracted and separated from the reaction product fluid by phase separation. By the practice of this invention, it is now possible to separate the desired product, along with any organophosphorus ligand degradation products and reaction byproducts, from the reaction product fluid without the need to use vaporization separation and the harsh conditions associated therewith. This invention provides a highly desirable separation method which prevents and/or lessens degradation of the organophosphorus ligand and deactivation of the catalyst as occur under harsh conditions with vaporization separation. This invention also provides a highly desirable separation method which prevents and/or lessens the buildup of organophosphorus ligand degradation products and reaction byproducts in the reaction product fluid.

This invention relates in part to a process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products, one or more nonpolar solvents and one or more polar solvents, wherein said process comprises (1) supplying said reaction product fluid from a reaction zone to a separation zone, (2) mixing said reaction product fluid in said separation zone to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts, said one or more products and said one or more polar solvents, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, (4) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents, (5) recovering said one or more organophosphorus ligand degradation products, said one or more reaction byproducts and said one or more products from said one or more polar solvents, and (6) supplying from said separation zone to said reaction zone and/or said separation zone one or more recycle streams comprising said one or more polar solvents; wherein (i) the selectivity of the nonpolar phase for the organophosphorus ligand with respect to the one or more products is expressed by the following partition coefficient ratio Ef1:

$$Ef1 = \frac{\text{Partition coefficient } Kp1 \text{ of organophosphorus ligand}}{\text{Partition coefficient } Kp2 \text{ of one or more products}}$$

in which said partition coefficient Kp1 is the ratio of the concentration of organophosphorus ligand in the nonpolar phase after extraction to the concentration of organophosphorus ligand in the polar phase after extraction, said partition coefficient Kp2 is the ratio of the concentration of products in the nonpolar phase after extraction to the concentration of products in the polar phase after extraction, and said Ef1 is a value greater than about 2.5, (ii) the selectivity of the nonpolar phase for the organophosphorus ligand with respect to the one or more organophosphorus ligand degradation products is expressed by the following partition coefficient ratio Ef2:

$$Ef2 = \frac{\text{Partition coefficient } Kp1 \text{ of organophosphorus ligand}}{\text{Partition coefficient } Kp3 \text{ of one or more organophosphorus ligand degradation products}}$$

in which said partition coefficient Kp1 is as defined above, said partition coefficient Kp3 is the ratio of the concentration of organophosphorus ligand degradation products in the nonpolar phase after extraction to the concentration of organophosphorus ligand degradation products in the polar phase after extraction, and said Ef2 is a value greater than about 2.5, and (iii) the selectivity of the nonpolar phase for the organophosphorus ligand with respect to the one or more reaction byproducts is expressed by the following partition coefficient ratio Ef3:

$$Ef3 = \frac{\text{Partition coefficient } Kp1 \text{ of organophosphorus ligand}}{\text{Partition coefficient } Kp4 \text{ of one or more reaction byproducts}}$$

in which said partition coefficient Kp1 is as defined above, said partition coefficient Kp4 is the ratio of the concentration of reaction byproducts in the nonpolar phase after extraction to the concentration of reaction byproducts in the polar phase after extraction, and said Ef3 is a value greater than about 2.5.

This invention also relates in part to a process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products and one or more nonpolar solvents, wherein said process comprises (1) supplying said reaction product fluid from a reaction zone to a separation zone, (2) mixing said reaction product fluid in said separation zone with one or more polar solvents to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts, said one or more products and said one or more polar solvents, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, (4) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents, (5) recovering said one or more organophosphorus ligand degradation products, said one or more reaction byproducts and said one or more products from said one or more polar solvents, and (6) supplying from said separation zone to said reaction zone and/or said separation zone one or more recycle streams comprising said one or more polar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention further relates in part to a continuous process for producing one or more products comprising: (1) reacting in a reaction zone one or more reactants in the presence of a metal-organophosphorus ligand complex catalyst, optionally free organophosphorus ligand, one or more nonpolar solvents and one or more polar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products, said one or more nonpolar solvents and said one or more polar solvents; (2) supplying said reaction product fluid from said reaction zone to a separation zone, (3) mixing said reaction product fluid in said separation zone to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts, said one or more products and said one or more polar solvents, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, (5) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents, (6) recovering said one or more organophosphorus ligand degradation products, said one or more reaction byproducts and said one or more products from said one or more polar solvents, and (7) supplying from said separation zone to said reaction zone and/or said separation zone one or more recycle streams comprising said one or more polar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention yet further relates in part to a continuous process for producing one or more products comprising: (1) reacting in a reaction zone one or more reactants in the presence of a metal-organophosphorus ligand complex catalyst, optionally free organophosphorus ligand and one or more nonpolar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products and said one or more nonpolar solvents; (2) supplying said reaction product fluid from said reaction zone to a separation zone, (3) mixing said reaction product fluid in said separation zone with one or more polar solvents to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts, said one or more products and said one or more polar solvents, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, (5) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents, (6) recovering said one or more organophosphorus ligand degradation products, said one or more reaction byproducts and said one or more products from said one or more polar solvents, and (7) supplying from said separation zone to said reaction zone and/or said separation zone one or more recycle streams comprising said one or more polar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention relates in part to a process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products, one or more first nonpolar solvents and one or more second nonpolar solvents, wherein said process comprises (1) supplying said reaction product fluid from a reaction zone to a separation zone, (2) mixing said reaction product fluid in said separation zone to obtain by phase separation a nonpolar phase comprising said one or more unreacted reactants, said metal-organophosphorus ligand complex catalyst, said optionally free organophosphorus ligand, said one or more first nonpolar solvents and said one or more second nonpolar solvents and a polar phase comprising said one or more organophosphorus ligand degradation products, said one or more reaction byproducts and said one or more products, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (4) supplying from said separation zone to said reaction zone and/or said separation zone one or more recycle streams comprising said one or more unreacted reactants, said metal-organophosphorus ligand complex catalyst, said optionally free organophosphorus ligand, said one or more first nonpolar solvents and said one or more second nonpolar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention also relates in part to a process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products and one or more first nonpolar solvents, wherein said process comprises (1) supplying said reaction product fluid from a reaction zone to a separation zone, (2) mixing said reaction product fluid in said separation zone with one or more second nonpolar solvents to obtain by phase separation a nonpolar phase comprising said one or more unreacted reactants, said metal-organophosphorus ligand complex catalyst, said optionally free organophosphorus ligand, said one or more first nonpolar solvents and said one or more second nonpolar solvents and a polar phase comprising said one or more organophosphorus ligand degradation products, said one or more reaction byproducts and said one or more products, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (4) supplying from said separation zone to said reaction zone and/or said separation zone one or more recycle streams comprising said one or more unreacted reactants, said metal-organophosphorus ligand complex catalyst, said optionally free organophosphorus ligand, said one or more first nonpolar solvents and said one or more second nonpolar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention further relates in part to a continuous process for producing one or more products comprising: (1) reacting in a reaction zone one or more reactants in the presence of a metal-organophosphorus ligand complex catalyst, optionally free organophosphorus ligand, one or more first nonpolar solvents and one or more second nonpolar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products, said one or more first nonpolar solvents and said one or more second nonpolar solvents; (2) supplying said reaction product fluid from said reaction zone to a separation zone, (3) mixing said reaction product fluid in said separation zone to obtain by phase separation a nonpolar phase comprising said one or more unreacted reactants, said metal-organophosphorus ligand complex catalyst, said optionally free organophosphorus ligand, said one or more first nonpolar solvents and said one or more second nonpolar solvents and a polar phase comprising said one or more organophosphorus ligand degradation products, said one or more reaction byproducts and said one or more products, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (5) supplying from said separation zone to said reaction zone and/or said separation zone one or more recycle streams comprising said one or more unreacted reactants, said metal-organophosphorus ligand complex catalyst, said optionally free organophosphorus ligand, said one or more first nonpolar solvents and said one or more second nonpolar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention yet further relates in part to a continuous process for producing one or more products comprising: (1) reacting in a reaction zone one or more reactants in the presence of a metal-organophosphorus ligand complex catalyst, optionally free organophosphorus ligand and one or more first nonpolar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products and said one or more first nonpolar solvents; (2) supplying said reaction product fluid from said reaction zone to a separation zone, (3) mixing said reaction product fluid in said separation zone with one or more second nonpolar solvents to obtain by phase separation a nonpolar phase comprising said one or more unreacted reactants, said metal-organophosphorus ligand complex catalyst, said optionally free organophosphorus ligand, said one or more first nonpolar solvents and said one or more second nonpolar solvents and a polar phase comprising said one or more organophosphorus ligand degradation products, said one or more reaction byproducts and said one or more products, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (5) supplying from said separation zone to said reaction zone and/or said separation zone one or more recycle streams comprising said one or more unreacted reactants, said metal-organophosphorus ligand complex catalyst, said optionally free organophosphorus ligand, said one or more first nonpolar solvents and said one or more second nonpolar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention relates in part to a process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products and one or more nonpolar solvents, wherein said process comprises (1) supplying said reaction product fluid from a reaction zone to a separation zone, (2) mixing said reaction product fluid in said separation zone to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts and said one or more products, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (4) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

This invention also relates in part to a continuous process for producing one or more products comprising: (1) reacting in a reaction zone one or more reactants in the presence of a metal-organophosphorus ligand complex catalyst, optionally free organophosphorus ligand and one or more nonpolar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products and said one or more nonpolar solvents; (2) supplying said reaction product fluid from said reaction zone to a separation zone, (3) mixing said reaction product fluid in said separation zone to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts and said one or more products, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (5) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents; wherein (i) the selectivity of the nonpolar phase for the organophosphorus ligand with respect to the one or more products is expressed by the partition coefficient ratio Ef1 defined above which is a value greater than about 2.5, (ii) the selectivity of the nonpolar phase for the organophosphorus ligand with respect to the one or more organophosphorus ligand degradation products is expressed by the partition coefficient ratio Ef2 defined above which is a value greater than about 2.5, and (iii) the selectivity of the nonpolar phase for the organophosphorus ligand with respect to the one or more reaction byproducts is expressed by the partition coefficient ratio Ef3 defined above which is a value greater than about 2.5.

DETAILED DESCRIPTION

The processes of this invention may be asymmetric or non-asymmetric, the preferred processes being non-asymmetric, and may be conducted in any continuous or semi-continuous fashion. The extraction and separation are critical features of this invention and may be conducted as described herein. The processing techniques used in this invention may correspond to any of the known processing techniques heretofore employed in conventional processes. Likewise, the manner or order of addition of the reaction ingredients and catalyst are also not critical and may be accomplished in any conventional fashion. As used herein, the term "reaction product fluid" is contemplated to include, but not limited to, a reaction mixture containing an amount of any one or more of the following: (a) a metal-organophosphorus ligand complex catalyst, (b) free organophosphorus ligand, (c) product(s), organophosphorus ligand degradation product(s) and byproduct(s) formed in the reaction, (d) unreacted reactant(s), and (e) solvent(s). As used herein, the term "organophosphorus ligand degradation products" is contemplated to include, but not limited to, any and all products resulting from the degradation of free organophosphorus ligand and organophosphorus ligand complexed with metal, e.g., phosphorus-containing acids, aldehyde acids, and the like. As used herein, the term "reaction byproducts" is contemplated to include, but not limited to, any and all byproducts resulting from the reaction of one or more reactants to give one or more products, e.g., product dimers, product trimers, isomerization products, hydrogenation products, and the like.

This invention (encompasses the carrying out of known conventional syntheses in a conventional fashion and the carrying out of extractions and separations in accordance with this invention. By the practice of this invention, it is now possible to extract and separate the one or more products, organophosphorus ligand degradation products and reaction byproducts from the metal-organophosphorus ligand complex catalyst and unreacted reactants without the need to use vaporization separation and the harsh conditions associated therewith.

Illustrative processes include, for example, hydroformylation, hydroacylation (intramolecular and intermolecular), hydrocyanation, hydroamidation, hydroesterification, aminolysis, alcoholysis, hydrocarbonylation, reductive hydroformylation, hydrogenation, olefin oligomerization, hydroxycarbonylation, carbonylation, olefin isomerization, transfer hydrogenation and the like. Preferred processes involve the reaction of organic compounds with carbon monoxide, or with carbon monoxide and a third reactant, e.g., hydrogen, or with hydrogen cyanide, in the presence of a catalytic amount of a metal-organophosphorus ligand complex catalyst. The most preferred processes include hydroformylation, hydrocyanation, hydrocarbonylation, hydroxycarbonylation and carbonylation.

Hydroformylation can be carried out in accordance with conventional procedures known in the art. For example, aldehydes can be prepared by reacting an olefinic compound, carbon monoxide and hydrogen under hydroformylation conditions in the presence of a metal-organophosphorus ligand complex catalyst described herein. Alternatively, hydroxyaldehydes can be prepared by reacting an epoxide, carbon monoxide and hydrogen under hydroformylation conditions in the presence of a metal-organophosphorus ligand complex catalyst described herein. The hydroxyaldehyde can be hydrogenated to a diol, e.g., hydroxypropionaldehyde can be hydrogenated to propanediol. Hydroformylation processes are described more fully hereinbelow.

Intramolecular hydroacylation can be carried out in accordance with conventional procedures known in the art. For example, aldehydes containing an olefinic group 3 to 7 carbons removed can be converted to cyclic ketones under hydroacylation conditions in the presence of a metal-organophosphorus ligand complex catalyst described herein.

Intermolecular hydroacylation can be carried out in accordance with conventional procedures known in the art. For example, ketones can be prepared by reacting an olefin and an aldehyde under hydroacylation conditions in the presence of a metal-organophosphorus ligand complex catalyst described herein.

Hydrocyanation can be carried out in accordance with conventional procedures known in the art. For example, nitrile compounds can be prepared by reacting an olefinic compound and hydrogen cyanide under hydrocyanation conditions in the presence of a metal-organophosphorus ligand complex catalyst described herein. A preferred hydrocyanation process involves reacting a nonconjugated acyclic aliphatic monoolefin, a monoolefin connected to an ester group, e.g., methyl pent-2-eneoate, or a monoolefin conjugated to a nitrile group, e.g., 2-pentenenitrile, with a source of hydrogen cyanide in the presence of a catalyst precursor composition comprising zero-valent nickel and a bidentate phosphite ligand to produce a terminal organonitrile, e.g., adiponitrile, alkyl 5-cyanovalerate or 3-(perfluoroalkyl) propionitrile. Preferably, the reaction is carried out in the presence of a Lewis acid promoter. Illustrative hydrocyanation processes are disclosed in U.S. Pat. No. 5,523,453 and WO 95/14659, the disclosures of which are incorporated herein by reference.

Hydroamidation can be carried out in accordance with conventional procedures known in the art. For example, amides can be prepared by reacting an olefin, carbon monoxide and a primary or secondary amine or ammonia under hydroamidation conditions in the presence of a metal-organophosphorus ligand complex catalyst described herein.

Hydroesterification can be carried out in accordance with conventional procedures known in the art. For example, esters can be prepared by reacting an olefin, carbon monoxide and an alcohol under hydroesterification conditions in the presence of a metal-organophosphorus ligand complex catalyst described herein.

Aminolysis can be carried out in accordance with conventional procedures known in the art. For example, amines can be prepared by reacting an olefin with a primary or secondary amine under aminolysis conditions in the presence of a metal-organophosphorus ligand complex catalyst described herein.

Alcoholysis can be carried out in accordance with conventional procedures known in the art. For example, ethers can be prepared by reacting an olefin with an alcohol under alcoholysis conditions in the presence of a metal-organophosphorus ligand complex catalyst described herein.

Hydrocarbonylation can be carried out in accordance with conventional procedures known in the art. For example, alcohols can be prepared by reacting an olefinic compound, carbon monoxide, hydrogen and a promoter under hydrocarbonylation conditions in the presence of a metal-organophosphorus ligand complex catalyst described herein.

Reductive hydroformylation can be carried out in accordance with conventional procedures known in the art. For example, alcohols can be prepared by reacting an olefinic compound, carbon monoxide and hydrogen under reductive hydroformylation conditions in the presence of a metal-organophosphorus ligand complex catalyst described herein.

Hydrogenation can be carried out in accordance with conventional procedures known in the art. For example, alcohols can be prepared by reacting an aldehyde under hydrogenation conditions in the presence of a metal-organophosphorus ligand complex catalyst described herein.

Olefin oligomerization can be carried out in accordance with conventional procedures known in the art. For example, higher olefins can be prepared by reacting an olefin under oligomerization conditions in the presence of a metal-organophosphorus ligand complex catalyst described herein.

Hydroxycarbonylation can be carried out in accordance with conventional procedures known in the art. For example, acids can be prepared by reacting an olefinic compound, carbon monoxide, water and a promoter under hydroxycarbonylation conditions in the presence of a metal-organophosphorus ligand complex catalyst described herein.

Carbonylation can be carried out in accordance with conventional procedures known in the art. For example, lactones can be prepared by treatment of allylic alcohols with carbon monoxide under carbonylation conditions in the presence of a metal-organophosphorus ligand complex catalyst described herein.

Isomerization can be carried out in accordance with conventional procedures known in the art. For example, allylic alcohols can be isomerized under isomerization conditions to produce aldehydes in the presence of a metal-organophosphorus ligand complex catalyst described herein.

Transfer hydrogenation can be carried out in accordance with conventional procedures known in the art. For example, alcohols can be prepared by reacting a ketone and an alcohol under transfer hydrogenation conditions in the presence of a metal-organophosphorus ligand complex catalyst described herein.

The permissible starting material reactants encompassed by the processes of this invention are, of course, chosen depending on the particular process desired. Such starting materials are well known in the art and can be used in conventional amounts in accordance with conventional methods. Illustrative starting material reactants include, for example, substituted and unsubstituted aldehydes (intramolecular hydroacylation), olefins (hydroformylation, carbonylation, hydrocarbonylation, reductive hydroformylation, intermolecular hydroacylation, hydrocyanation, hydroamidation, hydroesterification, aminolysis, alcoholysis), ketones (transfer hydrogenation), epoxides (hydroformylation, hydrocyanation), alcohols (carbonylation) and the like. Illustrative of suitable reactants for effecting the processes of this invention are set out in Kirk-Othmer, Encyclopedia of Chemical Technology, Fourth Edition, 1996, the pertinent portions of which are incorporated herein by reference.

Illustrative metal-organophosphorus ligand complex catalysts employable in the processes encompassed by this invention as well as methods for their preparation are well known in the art and include those disclosed in the below mentioned patents. In general such catalysts may be preformed or formed in situ as described in such references and consist essentially of metal in complex combination with an organophosphorus ligand. The active species may also contain carbon monoxide and/or hydrogen directly bonded to the metal.

The catalyst useful in the processes includes a metal-organophosphorus ligand complex catalyst which can be optically active or non-optically active. The permissible metals which make up the metal-organophosphorus ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Other permissible metals include Group 11 metals selected from copper (Cu), silver (Ag), gold (Au) and mixtures thereof, and also Group 6 metals selected from chromium (Cr), molybdenum (Mo), tungsten (W) and mixtures thereof. Mixtures of metals from Groups 6, 8, 9, 10 and 11 may also be used in this invention. The permissible organophosphorus ligands which make up the metal-organophosphorus ligand complexes and free organophosphorus ligand include organophosphines, e.g., bisphosphines and triorganophosphines, and organophosphites, e.g., mono-, di-, tri- and polyorganophosphites. Other permissible organophosphorus ligands include, for example, organophosphonites, organophosphinites, organophosphorus amides and the like. Mixtures of such ligands may be employed if desired in the metal-organophosphorus ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-organophosphorus ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the organophosphorus ligand and carbon monoxide and/or hydrogen when used.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorus ligands employable herein may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_6H_5CN$, $CH_3CN$, NO, $NH_3$, pyridine, $(C_2H_5)_3N$, monoolefins, diolefins and triolefins, tetrahydrofuran, and the like. It is of course to be understood that the complex species are preferably free of any additional organic ligand or anion that might poison the catalyst or have an undue adverse effect on catalyst performance. It is preferred in the metal-organophosphorus ligand complex catalyzed processes, e.g., hydroformylation, that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one organophosphorus-containing molecule complexed per one molecule of metal, e.g., rhodium. For instance, it is considered that the catalytic species of the preferred catalyst employed in a hydroformylation reaction may be complexed with carbon monoxide and hydrogen in addition to the organophosphorus ligands in view of the carbon monoxide and hydrogen gas employed by the hydroformylation reaction.

The organophosphines and organophosphites that may serve as the ligand of the metal-organophosphorus ligand complex catalyst and/or free ligand of the processes of this invention may be of the achiral (optically inactive) or chiral (optically active) type and are well known in the art. By "free ligand" is meant ligand that is not complexed with (tied to or bound to) the metal, e.g., metal atom, of the complex catalyst. As noted herein, the processes of this invention and especially the hydroformylation process may be carried out in the presence of free organophosphorus ligand. Achiral organophosphines and organophosphites are preferred.

Among the organophosphines that may serve as the ligand of the metal-organophosphine complex catalyst and/or free organophosphine ligand of the reaction mixture starting materials are triorganophosphines, triaLkylphosphines, alkyldiarylphosphines, dialkylarylphosphines, dicycloalkylarylphosphines, cycloalkyldiarylphosphines, trialkylphosphines, trialkarylphosphines, tricycloalkylphosphines, and triarylphosphines, alkyl and/or aryl bisphosphines and bisphosphine mono oxides, and the like. Of course any of the hydrocarbon radicals of such tertiary non-ionic organophosphines may be substituted if desired, with any suitable substituent that does not unduly adversely affect the desired result of the hydroformylation reaction. The organophosphine ligands employable in the reactions and/or methods for their preparation are known in the art.

Illustrative triorganophosphine ligands may be represented by the formula:

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, for example, alkyl radicals, alkoxy radicals, silyl radicals such as —Si$(R^2)_3$; amino radicals such as —N$(R^2)_2$; acyl radicals such as —C(O)$R^2$; carboxy radicals such as —C(O)O$R^2$; acyloxy radicals such as —OC(O)$R^2$; amido radicals such as —C(O)N$(R^2)_2$ and —N$(R^2)$C(O)$R^2$; sulfonyl radicals such as —SO$_2R^2$; ether radicals such as —O$R^2$; sulfinyl radicals such as —SO$R^2$; sulfenyl radicals such as —S$R^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —N$(R^2)_2$, each $R_2$ taken together can also represent a divalent bridging group that forms a heterocyclic radical with the nitrogen atom and in amido substituents such as C(O)N$(R^2)_2$ and —N$(R^2)$C(O)$R^2$ each —$R^2$ bonded to N can also be hydrogen. Illustrative alkyl radicals include, for example, methyl, ethyl, propyl, butyl and the like. Illustrative aryl radicals include, for example, phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, for example, tributylphosphine, trioctylphosphine, triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine as well as the alkali and alkaline earth metal salts of sulfonated triphenylphosphines, for example, of (tri-m-sulfophenyl)phosphine and of (m-sulfophenyl) diphenyl-phosphine and the like.

More particularly, illustrative metal-organophosphine complex catalysts and illustrative free organophosphine ligands include, for example, those disclosed in U.S. Pat. Nos. 3,527,809; 4,148,830; 4,247,486; 4,283,562; 4,400,548; 4,482,749 and 4,861,918, the disclosures of which are incorporated herein by reference.

Among the organophosphites that may serve as the ligand of the metal-organophosphite complex catalyst and/or free organophosphite ligand of the reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

(II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306, the disclosure of which is incorporated herein by reference.

Representative diorganophosphites may include those having the formula:

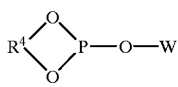

(III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, for example, alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, for example, in U.S. Pat. Nos. 3,415,906 and 4,567,302 and the like, the disclosures of which are incorporated herein by reference. Illustrative divalent aromatic radicals include, for example, arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, for example, in U.S. Pat. Nos. 4,599,206 and 4,717,775, and the like, the disclosures of which are incorporated herein by reference.

Representative of a more preferred class of diorganophosphites are those of the formula:

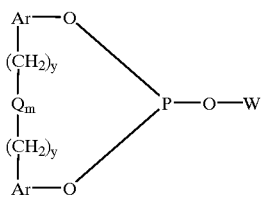

(IV)

wherein W is as defined above, each Ar is the same or different and represents a substituted or unsubstituted aryl radical, each y is the same or different and is a value of 0 or 1, Q represents a divalent bridging group selected from —C($R^5$)$_2$—, —O—, —S—, —N$R^6$—, Si($R^7$)$_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, for example, in U.S. Pat. Nos. 4,599,206, 4,717,775 and 4,835,299, the disclosures of which are incorporated herein by reference.

Representative triorganophosphites may include those having the formula:

(V)

wherein each $R^8$ is the same or different and is a substituted or unsubstituted monovalent hydrocarbon radical e.g., an alkyl, cycloalkyl, aryl, alkaryl and aralkyl radicals which may contain from 1 to 24 carbon atoms. Suitable hydrocarbon radicals may contain from 1 to 24 carbon atoms or greater and may include those described above for $R^1$ in formula (I). Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, tri-n-propyl phosphite, tri-n-butyl phosphite, tri-2-ethylhexyl phosphite, tri-n-octyl phosphite, tri-n-dodecyl phosphite, tri-o-tolyl phsophite, dimethylphenyl phosphite, diethylphenyl phosphite, methyldiphenyl phosphite, ethyldiphenyl phosphite, triphenyl phosphite, tri-naphthyl phosphite, bis(3,6,8-tri-t-butyl-2-naphthyl) methylphosphite, bis(3,6,8-tri-t-butyl-2-naphthyl) cyclohexylphosphite, tris(3,6-di-t-butyl-2-naphthyl) phosphite, bis(3,6,8-tri-t-butyl-2-naphthyl)(4-biphenyl) phosphite, bis(3,6,8-tri-t-butyl-2-naphthyl)phenylphosphite, bis(3,6,8-tri-t-butyl-2-naphthyl)(4-benzoylphenyl) phosphite, bis(3,6,8-tri-t-butyl-2-naphthyl)(4-sulfonylphenyl)phosphite, and the like. A preferred triorganophosphite is triphenylphosphite. Such triorganophosphites are described in greater detail, for example, in U.S. Pat. Nos. 3,527,809 and 5,277,532, the disclosures of which are incorporated herein by reference.

Representative organopolyphosphites contain two or more tertiary (trivalent) phosphorus atoms and may include those having the formula:

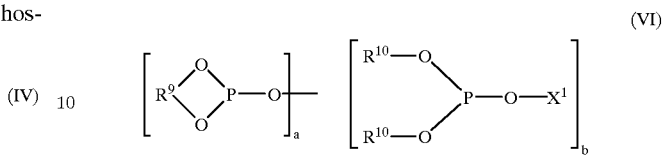

(VI)

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-Qm-alkylene, cycloalkylene, arylene, bisarylene, arylene-alkylene, and arylene-(CH$_2$)y-Qm-(CH$_2$)y-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and European Patent Application Publication No. 662,468, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

(VII)

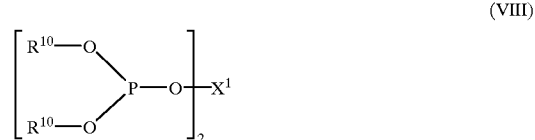

(VIII)

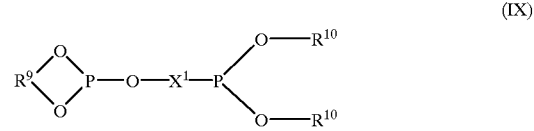

(IX)

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Organophosphite ligands of such Formulas (VI) to (IX) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

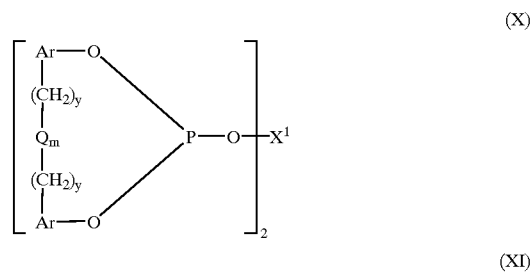

(X)

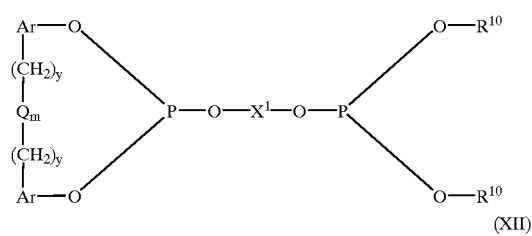

(XI)

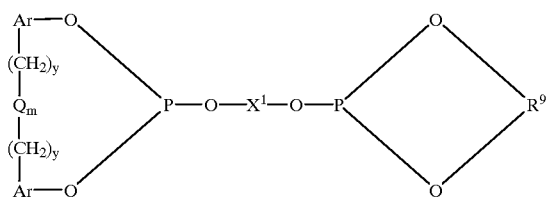

(XII)

wherein Ar, Q, $R^9$, $R^{10}$, $X^1$, m and y are as defined above. Most preferably $X^1$ represents a divalent aryl-$(CH_2)_y$—$(Q)_m$—$(CH_2)_y$-aryl radical wherein each y individually has a value of 0 or 1; m has a value of 0 or 1 and Q is —O—, —S— or —$C(R^5)_2$- wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (II) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Of course any of the $R^3$, $R^4$, $R^8$, $R^9$, $R^{10}$, $X^1$, $X^2$, W, Q and Ar radicals of such organophosphites of formulas (II) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —$Si(R^{12})_3$; amino radicals such as —$N(R^{12})_2$; phosphine radicals such as -aryl-$P(R^{12})_2$; acyl radicals such as —$C(O)R^{12}$; acyloxy radicals such as —$OC(O)R^{12}$; amido radicals such as —$CON(R^{12})_2$ and —$N(R^{12})COR^{12}$; sulfonyl radicals such as —$SO_2R^{12}$; alkoxy radicals such as —$OR^{12}$; sulfinyl radicals such as —$SOR^{12}$; sulfenyl radicals such as —$SR^{12}$; phosphonyl radicals such as —$P(O)(R^{12})_2$; as well as, halogen, nitro, cyano, trifluoromethyl, hydroxy radicals, and the like, wherein each $R^{12}$ radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —$N(R^{12})_2$ each $R^{12}$ taken together can also represent a divalent bridging group that forms a heterocyclic radical with the nitrogen atom, and in amido substituents such as —$C(O)N(R^{12})_2$ and —$N(R^{12})COR^{12}$ each $R^{12}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —$OCH_2CH_2OCH_3$, —$(OCH_2CH_2)_2OCH_3$, —$(OCH_2CH_2)_3OCH_3$, and the like; aryloxy radicals such as phenoxy and the like; as well as silyl radicals such as —$Si(CH_3)_3$, —$Si(OCH_3)_3$, —$Si(C_3H_7)_3$, and the like; amino radicals such as —$NH_2$, —$N(CH_3)_2$, —$NHCH_3$, —$NH(C_2H_5)$, and the like; arylphosphine radicals such as —$P(C_6H_5)_2$, and the like; acyl radicals such as —$C(O)CH_3$, —$C(O)C_2H_5$, —$C(O)C_6H_5$, and the like; carbonyloxy radicals such as —$C(O)OCH_3$ and the like; oxycarbonyl radicals such as —$O(CO)C_6H_5$, and the like; amido radicals such as —$CONH_2$, —$CON(CH_3)_2$, —$NHC(O)CH_3$, and the like; sulfonyl radicals such as —$S(O)_2C_2H_5$ and the like; sulfinyl radicals such as —$S(O)CH_3$ and the like; sulfenyl radicals such as —$SCH_3$, —$SC_2H_5$, —$SC_6H_5$, and the like; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, and the like.

Specific illustrative examples of organophosphorus ligands are described in copending U.S. Pat. No. 5,786,517, the disclosure of which is incorporated herein by reference.

The metal-organophosphorus ligand complex catalysts are preferably in homogeneous form. For instance, preformed rhodium hydrido-carbonyl-organophosphorus ligand catalysts may be prepared and introduced into the reaction mixture of a particular process. More preferably, the metal-organophosphorus ligand complex catalysts can be derived from a rhodium catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst.

As noted above, the organophosphorus ligands can be employed as both the ligand of the metal-organophosphorus ligand complex catalyst, as well as, the free organophosphorus ligand that can be present in the reaction medium of the processes of this invention. In addition, it is to be understood that while the organophosphorus ligand of the metal-organophosphorus ligand complex catalyst and any excess free organophosphorus ligand preferably present in a given process of this invention are normally the same type of ligand, different types of organophosphorus ligands, as well as, mixtures of two or more different organophosphorus ligands may be employed for each purpose in any given process, if desired.

The amount of metal-organophosphorus ligand complex catalyst present in the reaction medium of a given process of this invention need only be that minimum amount necessary to provide the given metal concentration desired to be employed and which will furnish the basis for at least that catalytic amount of metal necessary to catalyze the particular process desired. In general, metal concentrations in the range of from about 1 part per million to about 10,000 parts per million, calculated as free metal, and ligand to metal mole ratios in the catalyst solution ranging from about 1:1 or less to about 200:1 or greater, should be sufficient for most processes.

As noted above, in addition to the metal-organophosphorus ligand complex catalysts, the processes of this invention and especially the hydroformylation process can be carried out in the presence of free organophosphorus ligand. While the processes of this invention may be carried out in any excess amount of free organophosphorus ligand desired, the employment of free organophosphorus ligand may not be absolutely necessary. Accordingly, in general, amounts of ligand of from about 1.1 or less to about 200, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the process, at any time and in any suitable manner, to maintain a predetermined level of free ligand in the reaction medium.

The permissible reaction conditions employable in the processes of this invention are, of course, chosen depending on the particular syntheses desired. Such process conditions are well known in the art. All of the processes of this invention can be carried out in accordance with conventional procedures known in the art. Illustrative reaction conditions for conducting the processes of this invention are described, for example, in Kirk-Othmer, Encyclopedia of Chemical Technology, Fourth Edition. 1996, the pertinent portions of which are incorporated herein by reference. Depending on the particular process, operating temperatures may range from about −80° C. or less to about 500° C. or greater and operating pressures can range from about 1 psig or less to about 10,000 psig or greater.

The processes of this invention are conducted for a period of time sufficient to produce the desired products. The exact reaction time employed is dependent, in part, upon factors such as temperature, pressure, nature and proportion of starting materials, and the like. The reaction time will normally be within the range of from about one-half to about 200 hours or more, and preferably from less than about one to about 10 hours.

The processes of this invention are useful for preparing substituted and unsubstituted optically active and non-optically active compounds. Illustrative compounds prepared by the processes of this invention include, for example, substituted and unsubstituted alcohols or phenols; amines; amides; ethers or epoxides; esters; ketones; aldehydes; and nitriles. Illustrative of suitable optically active and non-optically active compounds which can be prepared by the processes of this invention (including starting material compounds as described hereinabove) include those permissible compounds which are described in Kirk-Othmer, Encyclopedia of Chemical Technology, Fourth Edition, 1996, the pertinent portions of which are incorporated herein by reference, and The Merck Index, An Encyclopedia of Chemicals, Drugs and Biologicals, Eleventh Edition, 1989, the pertinent portions of which are incorporated herein by reference.

As indicated above, the processes of this invention are conducted in the reaction zone in the presence of a nonpolar solvent and a polar solvent, or in the presence of a nonpolar solvent followed by mixing with a polar solvent prior to the separation zone, or in the presence of a nonpolar solvent followed by mixing with a second nonpolar solvent prior to the separation zone. Depending on the particular catalyst and reactants employed, suitable nonpolar solvents include, for example, alkanes, cycloalkanes, alkenes, alkadienes, aldehydes, ketones, ethers, esters, amines, aromatics, silanes, silicones, carbon dioxide, and the like. Examples of unsuitable nonpolar solvents include fluorocarbons and fluorinated hydrocarbons. These are undesirable due to their high cost, risk of environmental pollution, and the potential of forming multiphases. In an embodiment, the one or more reactants, metal-organophosphorus ligand complex catalyst, and optionally free organophosphorus ligand exhibit sufficient solubility in the nonpolar solvent such that phase transfer agents or surfactants are not required.

Mixtures of one or more different nonpolar solvents may be employed if desired. The amount of nonpolar solvent employed is not critical to the subject invention and need only be that amount sufficient to provide the reaction medium with the particular metal concentration desired for a given process. In general, the amount of nonpolar solvent employed may range from about 5 percent by weight up to about 99 percent by weight or more based on the total weight of the reaction mixture.

Illustrative nonpolar solvents useful in this invention include, for example, propane, 2,2-dimethylpropane, butane, 2,2-dimethylbutane, pentane, isopropyl ether, hexane, triethylamine, heptane, octane, nonane, decane, isobutyl isobutyrate, tributylamine, undecane, 2,2,4-trimethylpentyl acetate, isobutyl heptyl ketone, butadiene, diisobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, dodecene, tetradecene, and heptadecanal. The solubility parameters of illustrative nonpolar solvents are given in the Table below.

TABLE

Solubility Parameters of Illustrative Non-Polar Solvents

| Non-Polar Solvent | δSolvent $(cal/cm^3)^{1/2}$ | δSolvent $(kJ/m^3)^{1/2}$ |
|---|---|---|
| Propane | 5.76 | 373 |
| 2,2-Dimethylpropane | 6.10 | 395 |
| Butane | 6.58 | 426 |
| 2,2-Dimethylbutane | 6.69 | 433 |
| Pentane | 7.02 | 454 |
| Isopropyl Ether | 7.06 | 457 |
| Hexane | 7.27 | 470 |
| Triethylamine | 7.42 | 480 |
| Heptane | 7.50 | 485 |
| Octane | 7.54 | 488 |
| Nonane | 7.64 | 494 |
| Decane | 7.72 | 499 |
| Isobutyl Isobutyrate | 7.74 | 501 |
| Tributylamine | 7.76 | 502 |
| Undecane | 7.80 | 505 |
| 2,2,4-Trimethylpentyl Acetate | 7.93 | 513 |
| Isobutyl Heptyl Ketone | 7.95 | 514 |
| Diisobutyl Ketone | 8.06 | 521 |
| Cyclopentane | 8.08 | 523 |
| Cyclohexane | 8.19 | 530 |
| n-Nonylbenzene | 8.49 | 549 |
| n-Octylbenzene | 8.56 | 554 |
| n-Butylbenzene | 8.57 | 554 |
| p-Xylene | 8.83 | 571 |
| Ethylbenzene | 8.84 | 572 |
| 1,3,5-Trimethylbenzene | 8.84 | 572 |
| m-Xylene | 8.88 | 574 |
| Toluene | 8.93 | 578 |
| o-Xylene | 9.06 | 586 |

The desired products of this invention can be selectively recovered by extraction and phase separation in a polar solvent. As indicated above, the polar solvent can be present with the nonpolar solvent during the reaction or the reaction product fluid can be contacted with a polar solvent after the reaction. The desired reaction product is preferably extracted from the reaction product fluid through the use of an appropriate polar solvent such that any extraction of the one or more reactants, metal-organophosphorus ligand complex catalyst, and optionally free organophosphorus ligand from the reaction product fluid is minimized or eliminated. In an embodiment, the polar solvent is an aqueous mixture preferably containing up to about 8 weight percent water, more preferably less than about 6 weight percent water, and most preferably less than about 4 weight percent water. In this embodiment, the processes of this invention are considered to be essentially "non-aqueous" processes, which is to say, any water present in the reaction mediums is not present in an amount sufficient to cause either the particular reaction or said medium to be considered as encompassing a separate aqueous or water phase or layer in addition to the organic phases. Depending on the particular desired products, suitable polar solvents include, for example, nitrites, lactones, alkanols, cyclic acetals, water, pyrrolidones, formamides, sulfoxides and the like. In another embodiment, the polar solvent is other than a combination of a primary alkanol and water.

Mixtures of one or more different polar solvents may be employed if desired. The Hildebrand solubility parameter for the polar solvent or mixtures of one or more different polar solvents should be less than about 13.5 $(cal/cm^3)^{1/2}$ or 873 $(kJ/m^3)^{1/2}$, preferably less than about 13.0 $(cal/cm^3)^{1/2}$ or 841 $(kJ/m^3)^{1/2}$, and more preferably less than about 12.5 $(cal/cm^3)^{1/2}$ or 809 $(kJ/m^3)^{1/2}$. The amount of polar solvent employed is not critical to the subject invention and need only be that amount sufficient to extract the one or more products from the reaction product fluid for any given process. In general, the amount of polar solvent employed may range from about 5 percent by weight up to about 50 percent by weight or more based on the total weight of the reaction product fluid.

Illustrative polar solvents useful in this invention include, for example, propionitrile, 1,3-dioxolane, 3-methoxypropionitrile, N-methylpyrrolidone, N,N-dimethylformamide, 2-methyl-2-oxazoline, adiponitrile, acetonitrile, epsilon caprolactone, glutaronitrile, 3-methyl-2-oxazolidinone, water, dimethyl sulfoxide and sulfolane. For purposes of this invention, the one or more products may serve as the polar reaction solvent. The solubility parameters of illustrative polar solvents are given in the Table below.

TABLE

Solubility Parameters of Illustrative Polar Solvents

| Polar Solvent | δSolvent $(cal/cm^3)^{1/2}$ | δSolvent $(kJ/m^3)^{1/2}$ |
|---|---|---|
| Propionitrile | 10.73 | 694 |
| 1,3-Dioxolane | 11.33 | 733 |
| 3-Methoxypropionitrile | 11.37 | 735 |
| N-Methylpyrrolidone | 11.57 | 748 |
| N,N-Dimethylformamide | 11.76 | 761 |
| 2-Methyl-2-Oxazoline | 12.00 | 776 |
| Adiponitrile | 12.05 | 779 |
| Acetonitrile | 12.21 | 790 |
| E-Caprolactone | 12.66 | 819 |
| Sulfolane | 12.80 | 828 |
| Glutaronitrile | 13.10 | 847 |
| Dimethyl Sulfoxide | 13.10 | 847 |
| 3-Methyl-2-Oxazolidinone | 13.33 | 862 |
| Water | 23.53 | 1522 |

Extraction to obtain one phase comprising the one or more reactants, metal-organophosphorus ligand complex catalyst, optionally free organophosphorus ligand and nonpolar solvent and at least one other phase comprising one or more products and polar solvent is an equilibrium process. The relative volumes of the polar solvent (or extraction solution) and the nonpolar solvent or reaction product fluid in this extraction operation are determined in part by the solubility of the one or more reactants, metal-organophosphorus ligand complex catalyst, optionally free organophosphorus ligand and one or more products in the solvents used, and the amount of desired product to be extracted. For example, when the desired product is extracted, if the desired product to be extracted shows high solubility in the polar solvent and is present at a relatively low concentration in the reaction product fluid, it is possible to extract the desired product by using the polar solvent in a relatively small volume ratio to the reaction product fluid. The polar and nonpolar solvents described above may be used as extraction solvents.

Further, as the concentration of the desired product becomes high, it is usually required to increase the ratio of the polar solvent to the reaction product fluid for extracting the desired product from the reaction product fluid. When the desired product shows relatively low solubility in the polar solvent, the relative volume of the polar solvent or extraction solution will have to be increased. Generally, the volume ratio of the polar solvent or extraction solution to the reaction product fluid may be changed within a range of from about 20:1 to about 1:20.

In an embodiment, the products produced by the processes of this invention may contain sufficient polarity to make the products immiscible with the non-polar solvent. Phase separation may occur spontaneously prior to the separation zone or may be induced by a change in temperature or pressure or the addition of an additive, e.g., salt, or the evaporation of a solvent or combinations thereof. The addition of an external polar solvent to induce phase separation may not be required for certain processes of this invention.

Except as noted above, with respect to the extraction temperature, there is no merit in employing a temperature higher than the reaction temperature of the particular process, and desirable results can be obtained by employing an extraction temperature lower than the process reaction temperature. Depending on the particular process, extraction temperatures may range from about —80° C. or less to about 200° C. or greater.

The time for mixing the reaction product fluid with the polar solvent, i.e. the time before the phase separation, depends on the rate until the two-phases reach the equilibrium condition. Generally, such a time maybe varied from within one minute or less to a longer period of one hour or more.

The extraction process of this invention is in part an equilibrium process of an organophosphorus ligand dissolved in two separate liquid phases. The efficiency of this extraction process can be measured by a partition coefficient $Kp1$ of the organophosphorus ligand which is defined as follows:

$$Kp1 = \frac{\text{Concentration of organophosphorus ligand in the nonpolar phase after extraction}}{\text{Concentration of organophosphorus ligand in the polar phase after extraction}}$$

When the one or more desired products are partitioned between the polar phase and the nonpolar phase by the extraction process of this invention, the $Kp1$ value of the organophosphorus ligand can be maintained at a level greater than about 5, preferably greater than about 7.5, and more preferably greater than about 10, depending on the efficiency of the extraction process. If this $Kp1$ value is high, the organophosphorus ligand will preferentially distribute into the nonpolar phase. As used in $Kp1$, the concentration of organophosphorus ligand includes both free organophosphorus ligand and organophosphorus ligand complexed with the metal.

The extraction process of this invention is also in part an equilibrium process of one or more products dissolved in two separate liquid phases. The efficiency of this extraction process can be measured by a partition coefficient $Kp2$ of the one or more products which is defined as follows:

$$Kp2 = \frac{\text{Concentration of products in the nonpolar phase after extraction}}{\text{Concentration of products in the polar phase after extraction}}$$

When the one or more desired products are partitioned between the polar phase and the nonpolar phase by the extraction process of this invention, the $Kp2$ value of the products can be maintained at a level less than about 2, preferably less than about 1.5, and more preferably less than about 1, depending on the efficiency of the extraction process. If this $Kp2$ value is low, the products will preferentially distribute into the polar phase.

The extraction process of this invention is further in part an equilibrium process of one or more organophosphorus ligand degradation products dissolved in two separate liquid phases. The efficiency of this extraction process can be measured by a partition coefficient $Kp3$ of the one or more organophosphorus ligand degradation products which is defined as follows:

$$Kp3 = \frac{\text{Concentration of organophosphorus ligand degradation products in the nonpolar phase after extraction}}{\text{Concentration of organophosphorus ligand degradation products in the polar phase after extraction}}$$

When the one or more organophosphorus ligand degradation products are partitioned between the polar phase and the nonpolar phase by the extraction process of this invention, the $Kp3$ value of the organophosphorus ligand degradation products can be maintained at a level less than about 2, preferably less than about 1.5, and more preferably less than about 1, depending on the efficiency of the extraction process. If this $Kp3$ value is low, the organophosphorus ligand degradation products will preferentially distribute into the polar phase.

The extraction process of this invention is yet further in part an equilibrium process of one or more reaction byproducts dissolved in two separate liquid phases. The efficiency of this extraction process can be measured by a partition coefficient $Kp4$ of the one or more reaction byproducts which is defined as follows:

$$Kp4 = \frac{\text{Concentration of reaction byproducts in the nonpolar phase after extraction}}{\text{Concentration of reaction byproducts in the polar phase after extraction}}$$

When the one or more reaction byproducts are partitioned between the polar phase and the nonpolar phase by the extraction process of this invention, the $Kp4$ value of the reaction byproducts can be maintained at a level less than about 2, preferably less than about 1.5, and more preferably less than about 1, depending on the efficiency of the extraction process. If this $Kp4$ value is low, the reaction byproducts will preferentially distribute into the polar phase.

The extraction process of this invention is conducted in a manner such that three separation criteria are satisfied. The three criteria are referred to herein as extraction factors and are based on ratios of the partition coefficients defined above. The relationships embodied by the extraction factors include selectivity of the nonpolar phase for the organophosphorus ligand with respect to the product, selectivity of the nonpolar phase for the organophosphorus ligand with respect to the organophosphorus ligand degradation products, and selectivity of the nonpolar phase for the organophosphorus ligand with respect to the reaction byproducts. The three extraction factors are set out below.

The extraction factor defining selectivity of the nonpolar phase for the organophosphorus ligand with respect to the one or more products is a partition coefficient ratio as follows:

$$Ef1 = \frac{\text{Partition coefficient } Kp1 \text{ of organophosphorus ligand}}{\text{Partition coefficient } Kp2 \text{ of one or more products}}$$

The $Ef1$ value for the above ratio is maintained at a level greater than about 2.5, preferably greater than about 3.0, and more preferably greater than about 3.5, depending on the efficiency of the extraction process. If this Ef1 value is high, the extraction selectivity will be high.

The extraction factor defining selectivity of the nonpolar phase for the organophosphorus ligand with respect to the one or more organophosphorus ligand degradation products is a partition coefficient ratio as follows:

$$Ef2 = \frac{\text{Partition coefficient } Kp1 \text{ of organophosphorus ligand}}{\text{Partition coefficient } Kp3 \text{ of one or more organophosphorus ligand degradation products}}$$

The Ef2 value for the above ratio is maintained at a level greater than about 2.5, preferably greater than about 3.0, and more preferably greater than about 3.5, depending on the efficiency of the extraction process. If this Ef2 value is high, the extraction selectivity will be high.

The extraction factor defining selectivity of the nonpolar phase for the organophosphorus ligand with respect to the one or more reaction byproducts is a partition coefficient ratio as follows:

$$Ef3 = \frac{\text{Partition coefficient } Kp1 \text{ of organophosphorus ligand}}{\text{Partition coefficient } Kp4 \text{ of one or more reaction byproducts}}$$

The Ef3 value for the above ratio is maintained at a level greater than about 2.5, preferably greater than about 3.0, and more preferably greater than about 3.5, depending on the efficiency of the extraction process. If this Ef3 value is high, the extraction selectivity will be high.

The extraction process of this invention may be conducted in one or more stages. The exact number of extraction stages will be governed by the best compromise between capital costs and achieving high extraction efficiency and ease of operability, as well as the stability of the starting materials and the desired reaction product to the extraction conditions. Also, the extraction process of this invention may be conducted in a batch or continuous fashion. When conducted continuously, the extraction may be conducted in a cocurrent or countercurrent manner or factional countercurrent extraction may be used. Suitable fractional countercurrent extraction methods are disclosed in copending U.S. patent application Ser. Nos. (D-18040 and D-18041), filed on an even date herewith, the disclosures of which are incorporated herein by reference. In an embodiment, the reaction product fluid supplied from the reaction zone to the separation zone preferably contains at least 5 weight percent, preferably at least 10 weight percent, of one or more products.

In a preferred embodiment, when the reaction product fluid is supplied from the reaction zone to the separation zone, the reaction product fluid first passes through a vaporizer or distillation column or other separation apparatus to remove at least some product, reaction byproducts and/or unreacted reactants. At least a portion of the resulting reaction product fluid, depleted in product, reaction byproducts and/or unreacted reactants, then passes to the fractional countercurrent extractor. The separation prior to the fractional countercurrent extractor may remove essentially all products and a major amount of reaction byproducts and unreacted reactants. In another embodiment, the separation prior to the fractional countercurrent extractor may remove a major amount of reaction byproducts and unreacted reactants, and essentially all products pass to the fractional countercurrent extractor. The reaction product fluid can be a single liquid phase or it may form two partially miscible phases. The reaction product fluid may contain one or more solid phases. For purposes of this invention, the separation zone includes, but is not limited to, one or more fractional countercurrent extractors, one or more vaporizers, one or more distillation columns, one or more other separation apparatus, and permissible combinations thereof in parallel or in series. Preferably, an amount of one or more organophosphorus ligand degradation products, one or more reaction byproducts and one or more products are removed from the separation zone essentially equal to their rate of formation in the reaction product fluid in the reaction zone whereby the amount of one or more organophosphorus ligand degradation products, one or more reaction byproducts and one or more products in the reaction product fluid in the reaction zone is maintained at a predetermined level. In the embodiments involving intermediate separation by a vaporizer or distillation column or other separation apparatus, subsequent phase separation may occur by liquid-liquid phase separation, countercurrent extraction or fractional countercurrent extraction.

Illustrative types of extractors that may be employed in this invention include, for example, columns, centrifuges, mixer-settlers, and miscellaneous devices. Extractors that could be utilized include unagitated columns, e.g., spray, baffle tray and packed, agitated columns, e.g., pulsed, rotary agitated and reciprocating plate, mixer-settlers, e.g., pump-settler, static mixer-settler and agitated mixer-settler, centrifugal extractors, e.g., those produced by Robatel, Luwesta, deLaval, Dorr Oliver, Bird and Podbielniak, and miscellaneous extractors, e.g., the emulsion phase contactor and hollow-fiber membrane. A description of these devices can be found in the Handbook of Solvent Extraction, Krieger Publishing Company, Malabar, Fla., 1991, the disclosure of which is incorporated herein by reference. As used in this invention, the various types of extractors may be combined in any combination to effect the desired extraction.

Following the extraction, the desired products of this invention may be recovered by phase separation in which the polar phase comprising one or more products, along with any organophosphorus ligand degradation products and reaction byproducts, is separated from the nonpolar phase. The phase separation techniques may correspond to those techniques heretofore employed in conventional processes, and can be accomplished in the extractor or in a separated liquid-liquid separation device. Suitable liquid-liquid separation devices include, but are not limited to, coalescers, cyclones and centrifuges. Typical equipment used for liquid-liquid phase separation devices are described in the Handbook of Separation process Technology, ISBN 0-471-89558-X, John Wiley & Sons, Inc., 1987, the disclosure of which is incorporated herein be reference. Following phase separation in which a layer of the extraction fluid, e.g., polar solvent and one or more organophosphorus ligand degradation products, one or more reaction byproducts and one or more products, is separated from a layer of the remaining reaction product fluid, the desired products can then be separated from the undesired organophosphorus ligand degradation products and reaction byproducts by conventional methods such as distillation.

From a free energy standpoint, to attain dissolution or miscibility of a phosphorous containing ligand in a particular solvent, the enthalpy of mixing should be as small as possible. The enthalpy of mixing ($\Delta H_m$) can be approximated by the Hildebrand equation (1)

$$\Delta H_m = \Phi_S \Phi_L V(\delta_{Solvent} - \delta_{Ligand})^2 \quad (1)$$

using the solubility parameters of the solvent ($\delta_{Solvent}$) and ligand ($\delta_{Ligand}$), where V is the molar volume of the mixture, and $\Phi_S$ and $\Phi_L$ are the volume fractions of the solvent and ligand, respectively. Based on equation (1), the ideal solvent for a ligand would have the same solubility parameter as the ligand itself, so that $\Delta H_m = 0$. However, for each ligand there is a characteristic range originating from its solubility parameter which encloses all liquids that are solvents for the ligand. In general, a solvent or a solvent blend having a solubility parameter that is within two units of the solubility parameter of the ligand will dissolve the ligand; however, relatively large deviations from this value can sometimes occur, especially if there are strong hydrogen bonding interactions. Therefore, equation (2)

$$\delta_{Solvent} - \delta_{Ligand} < 2.0 (cal/cm^3)^{1/2} \quad (2)$$

can be used semi-quantitatively to determine whether a liquid is a good solvent for a given ligand. In equation (2), $\delta_{Solvent}$ and $\delta_{Ligand}$ represent the solubility parameters of the solvent and ligand respectively.

For purposes of this invention, the solubility parameters for solvents can be calculated from equation (3)

$$\delta_{Solvent} = (\Delta H_v - RT) d / MW \quad (3)$$

in which $\Delta H_v$ is the heat of vaporization, R is a gas constant, T is temperature in degrees absolute, d is the density of the solvent, and MW is molecular weight of the solvent. The solubility parameters for a wide variety of solvents have been reported by K. L. Hoy, "New Values of the Solubility Parameters from Vapor Pressure Data," Journal of Paint Technology, 42, (1970), 76.

The heat of vaporization for phosphorous containing compounds cannot be easily measured since many of these compounds decompose at higher temperatures. Furthermore, since many phosphorous containing compounds are solids at room temperature, measurements of density are not convenient. The solubility parameters, in units of $(cal/cm^3)^{1/2}$, for phosphorus containing ligands can be calculated using equation (4)

$$\delta_{Ligand} = (\Sigma F_T + 135.1)/(0.01211 + \Sigma N_i V_{1i}) 1000 \quad (4)$$

from group contribution theory as developed by (1) K. L. Hoy, "New Values of the Solubility Parameters from Vapor Pressure Data," Journal of Paint Technology, 42, (1970), 76, and (2) L. Constantinou, R. Gani, J. P. O'Connell, "Estimation of the Acentric Factor and the Liquid Molar Volume at 298 K Using a New Group Contribution Method," Fluid Phase Equilibria, 103, (1995), 11. In equation (4), $\Sigma F_T$ is the sum of all the group molar attraction constants, and $\Sigma N_i V_{1i}$ is the sum of all the first order liquid molar volume constants $V_{1i}$, which occur $N_i$ times. These methods have been expanded to include the group molar attraction constant of 79.4 $(cal/cm^3)^{1/2}$/mole and first order liquid molar volume constant of 0.0124 $m^3$/kmol for (>P-) derived from triphenylphosphine data found in T. E. Daubret, R. P. Danner, H. M. Sibul, and C. C. Stebbins, "DIPPR Data Compilation of Pure Compound Properties," Project 801, Sponsor Release, July 1995, Design Institute for Physical Property Data, AIChE, New York, N.Y.

The processes of this invention can be conducted in a batch or continuous fashion, with recycle of unconsumed starting materials if required. The reaction can be conducted in a plurality of reaction zones, in series or in parallel or it may be conducted batchwise or continuously in an elongated tubular zone or series of such zones. For example, a backmixed reactor may be employed in series with a multistaged reactor with the backmixed reactor being first. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can optionally be separated from the product by phase separation, and the starting materials then recycled back into the reaction zone.

At the conclusion of (or during) the processes of this invention, the desired products may be recovered from the reaction mixtures produced in the processes of this invention. For instance, in a continuous liquid catalyst recycle process the portion of the liquid reaction mixture (containing product, catalyst, etc.) removed from the reaction zone can be passed to a separation zone wherein the desired product can be extracted and separated via phase separation from the liquid reaction mixture, and further purified if desired. The remaining catalyst containing liquid reaction mixture may then be recycled back to the reaction zone as may if desired any other materials, e.g., unreacted reactants, together with any hydrogen and carbon monoxide dissolved in the liquid reaction after separation thereof from the product.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more reaction steps and more than one reactive stages. The exact number of reaction steps and reactive stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In a preferred embodiment, the hydrocarbonylation processes involve converting one or more substituted or unsubstituted olefins to one or more substituted or unsubstituted alcohols. In a preferred embodiment, the hydrocarbonylation processes involve converting one or more substituted or unsubstituted alkadienes to one or more substituted or unsubstituted unsaturated alcohols and/or converting one or more substituted or unsubstituted pentenals to one or more substituted or unsubstituted hydroxyaldehydes and/or diols. The hydrocarbonylation processes may be conducted in one or more steps or stages, preferably a one step process. As used herein, the term "hydrocarbonylation" is contemplated to include all permissible hydrocarbonylation processes which involve converting one or more substituted or unsubstituted olefins to one or more substituted or unsubstituted alcohols and/or converting one or more substituted or unsubstituted pentenals to one or more substituted or unsubstituted hydroxyaldehydes and/or diols. In a preferred embodiment, the hydrocarbonylation process comprises reacting one or more substituted or unsubstituted alkadienes, e.g., butadienes, with carbon monoxide and hydrogen in the presence of a metal-ligand complex catalyst, e.g., a metal-organophosphorus ligand complex catalyst, and a promoter and optionally free ligand to produce one or more substituted or unsubstituted unsaturated alcohols, e.g., penten-1-ols, and/or reacting one or more substituted or unsubstituted pentenals with carbon monoxide and hydrogen in the presence of a metal-ligand complex catalyst, e.g., a metal-organophosphorus ligand complex catalyst, and a promoter and optionally free ligand to produce one or more substituted or unsubstituted hydroxyaldehydes, e.g., 6-hydroxyhexanal. The alcohol product can then be recovered in accordance with the separation techniques of this invention. Preferred hydrocarbonylation processes useful in this invention are disclosed in U.S. Pat. No. 5,817,883, infra.

In another preferred embodiment, the reductive hydroformylation processes involve converting one or more substituted or unsubstituted olefins to one or more substituted or unsubstituted alcohols. In a preferred embodiment, the reductive hydroformylation processes involve converting one or more substituted or unsubstituted alkadienes to one or more substituted or unsubstituted unsaturated alcohols and/or converting one or more substituted or unsubstituted pentenals to one or more substituted or unsubstituted hydroxyaldehydes and/or diols. The reductive hydroformylation processes may be conducted in one or more steps or stages, preferably a one step process. As used herein, the term "reductive hydroformylation" is contemplated to include, but is not limited to, all permissible hydroformylation, hydrogenation and isomerization processes which involve converting one or more substituted or unsubstituted olefins to one or more substituted or unsubstituted alcohols and/or converting one or more substituted or unsubstituted pentenals to one or more substituted or unsubstituted hydroxyaldehydes and/or diols. In a preferred embodiment, the reductive hydroformylation process comprises reacting one or more substituted or unsubstituted alkadienes, e.g., butadienes, with carbon monoxide and hydrogen in the presence of a metal-ligand complex catalyst, e.g., a metal-organophosphorus ligand complex catalyst, and optionally free ligand to produce one or more substituted or unsubstituted unsaturated alcohols, e.g., penten-1-ols, and/or reacting one or more substituted or unsubstituted pentenals with carbon monoxide and hydrogen in the presence of a metal-ligand complex catalyst, e.g., a metal-organophosphorus ligand complex catalyst, and optionally free ligand to produce one or more substituted or unsubstituted hydroxyaldehydes, e.g., 6-hydroxyhexanal. The alcohol product can then be recovered in accordance with the separation techniques of this invention. Preferred reductive hydroformylation processes useful in this invention are disclosed in U.S. Pat. No. 5,821,389, infra.

In yet another preferred embodiment, the hydroformylation processes involve converting one or more substituted or unsubstituted olefins to one or more substituted or unsubstituted aldehydes. In a preferred embodiment, the hydroformylation processes involve converting one or more substituted or unsubstituted unsaturated alcohols to one or more substituted or unsubstituted hydroxyaldehydes and/or converting one or more substituted or unsubstituted unsaturated esters to one or more substituted or unsubstituted formylesters. The hydroformylation processes may be conducted in one or more steps or stages, preferably a one step process. As used herein, the term "hydroformylation" is contemplated to include all permissible hydroformylation processes which involve converting one or more substituted or unsubstituted olefins to one or more substituted or unsubstituted aldehydes. In a preferred embodiment, the hydroformylation process comprises reacting one or more substituted or unsubstituted alcohols, e.g., penten-1-ols, with carbon monoxide and hydrogen in the presence of a metal-ligand complex catalyst, e.g., a metal-organophosphorus ligand complex catalyst, and optionally free ligand to produce one or more substituted or unsubstituted hydroxyaldehydes, e.g., 6-hydroxyaldehyde. The aldehyde product can then be recovered in accordance with the separation techniques of this invention. Preferred hydroformylation processes useful in this invention are disclosed in U.S. Pat. Nos. 4,148,830; 4,593,127; 4,769,498; 4,717,775; 4,774,361; 4,885,401; 5,264,616; 5,288,918; 5,360,938; 5,364,950; 5,491,266; 5,731,472; 5,741,942; 5,763,679; 5,817,883; and 5,821,389; the disclosures of which are incorporated herein by reference. Other preferred hydroformylation processes useful in this invention are disclosed in copending U.S. patent application Ser. Nos. (D-17977, D-17978 and D-17979), the disclosures of which are incorporated herein by reference.

The products, e.g., aldehydes, produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, esterification, etherification, amination, alkylation, dehydrogenation, reduction, acylation, condensation, carboxylation, carbonylation, oxidation, cyclization, silylation and the like, including permissible combinations thereof. This invention is not intended to be limited in any manner by the permissible derivatization reactions or permissible derivatives of products.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

What is claimed is:

1. A process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products, one or more nonpolar solvents and one or more polar solvents, wherein said process comprises (1) supplying said reaction product fluid from a reaction zone to a separation zone, (2) mixing said reaction product fluid in said separation zone to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts, said one or more products and said one or more polar solvents, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, (4) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents, (5) recovering said one or more organophosphorus ligand degradation products, said one or more reaction byproducts and said one or more products from said one or more polar solvents, and (6) supplying from said separation zone to said reaction zone and/or said separation zone one or more recycle streams comprising said one or more polar solvents; wherein (i) the selectivity of the nonpolar phase for the organophosphorus ligand with respect to the one or more products is expressed by the following partition coefficient ratio Ef1:

$$Ef1 = \frac{\text{Partition coefficient } Kp1 \text{ of organophosphorus ligand}}{\text{Partition coefficient } Kp2 \text{ of one or more products}}$$

in which said partition coefficient Kp1 is the ratio of the concentration of organophosphorus ligand in the nonpolar phase after extraction to the concentration of organophosphorus ligand in the polar phase after extraction, said partition coefficient Kp2 is the ratio of the concentration of products in the nonpolar phase after extraction to the concentration of products in the polar phase after extraction, and said Ef1 is a value greater than about 2.5, (ii) the selectivity of the nonpolar phase for the organophosphorus ligand with respect to the one or more organophosphorus ligand degradation products is expressed by the following partition coefficient ratio Ef2:

$$Ef2 = \frac{\text{Partition coefficient } Kp1 \text{ of organophosphorus ligand}}{\text{Partition coefficient } Kp3 \text{ of one or more organophosphorus ligand degradation products}}$$

in which said partition coefficient Kp1 is as defined above, said partition coefficient Kp3 is the ratio of the concentration of organophosphorus ligand degradation products in the nonpolar phase after extraction to the concentration of organophosphorus ligand degradation products in the polar phase after extraction, and said Ef2 is a value greater than about 2.5, and (iii) the selectivity of the nonpolar phase for the organophosphorus ligand with respect to the one or more reaction byproducts is expressed by the following partition coefficient ratio Ef3:

$$Ef3 = \frac{\text{Partition coefficient } Kp1 \text{ of organophosphorus ligand}}{\text{Partition coefficient } Kp4 \text{ of one or more reaction byproducts}}$$

in which said partition coefficient Kp1 is as defined above, said partition coefficient Kp4 is the ratio of the concentration of reaction byproducts in the nonpolar phase after extraction to the concentration of reaction byproducts in the polar phase after extraction, and said Ef3 is a value greater than about 2.5.

2. A process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products and one or more nonpolar solvents, wherein said process comprises (1) supplying said reaction product fluid from a reaction zone to a separation zone, (2) mixing said reaction product fluid in said separation zone with one or more polar solvents to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts, said one or more products and said one or more polar solvents, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, (4) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents, (5) recovering said one or more organophosphorus ligand degradation products, said one or more reaction byproducts and said one or more products from said one or more polar solvents, and (6) supplying from said separation zone to said reaction zone and/or said separation zone one or more recycle streams comprising said one or more polar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

3. A continuous process for producing one or more products comprising: (1) reacting in a reaction zone one or more reactants in the presence of a metal-organophosphorus ligand complex catalyst, optionally free organophosphorus ligand, one or more nonpolar solvents and one or more polar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products, said one or more nonpolar solvents and said one or more polar solvents; (2) supplying said reaction product fluid from said reaction zone to a separation zone, (3) mixing said reaction product fluid in said separation zone to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts, said one or more products and said one or more polar solvents, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, (5) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents, (6) recovering said one or more organophosphorus ligand degradation products, said one or more reaction byproducts and said one or more products from said one or more polar solvents, and (7) supplying from said separation zone to said reaction zone and/or said separation zone one or more recycle streams comprising said one or more polar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

4. A continuous process for producing one or more products comprising: (1) reacting in a reaction zone one or more reactants in the presence of a metal-organophosphorus ligand complex catalyst, optionally free organophosphorus ligand and one or more nonpolar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products and said one or more nonpolar solvents; (2) supplying said reaction product fluid from said reaction zone to a separation zone, (3) mixing said reaction product fluid in said separation zone with one or more polar solvents to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts, said one or more products and said one or more polar solvents, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, (5) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents, (6) recovering said one or more organophosphorus ligand degradation products, said one or more reaction byproducts and said one or more products from said one or more polar solvents, and (7) supplying from said separation zone to said reaction zone and/or said separation zone one or more recycle streams comprising said one or more polar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

5. A process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products, one or more first nonpolar solvents and one or more second nonpolar solvents, wherein said process comprises (1) supplying said reaction product fluid from a reaction zone to a separation zone, (2) mixing said reaction product fluid in said separation zone to obtain by phase separation a nonpolar phase comprising said one or more unreacted reactants, said metal-organophosphorus ligand complex catalyst, said optionally free organophosphorus ligand, said one or more first nonpolar solvents and said one or more second nonpolar solvents and a polar phase comprising said one or more organophosphorus ligand degradation products, said one or more reaction byproducts and said one or more products, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (4) supplying from said separation zone to said reaction zone and/or said separation zone one or more recycle streams comprising said one or more unreacted reactants, said metal-organophosphorus ligand complex catalyst, said optionally free organophosphorus ligand, said one or more first nonpolar solvents and said one or more second nonpolar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

6. A process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products and one or more first nonpolar solvents, wherein said process comprises (1) supplying said reaction product fluid from a reaction zone to a separation zone, (2) mixing said reaction product fluid in said separation zone with one or more second nonpolar solvents to obtain by phase separation a nonpolar phase comprising said one or more unreacted reactants, said metal-organophosphorus ligand complex catalyst, said optionally free organophosphorus ligand, said one or more first nonpolar solvents and said one or more second nonpolar solvents and a polar phase comprising said one or more organophosphorus ligand degradation products, said one or more reaction byproducts and said one or more products, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (4) supplying from said separation zone to said reaction zone and/or said separation zone one or more recycle streams comprising said one or more unreacted reactants, said metal-organophosphorus ligand complex catalyst, said optionally free organophosphorus ligand, said one or more first nonpolar solvents and said one or more second nonpolar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

7. A continuous process for producing one or more products comprising: (1) reacting in a reaction zone one or more reactants in the presence of a metal-organophosphorus ligand complex catalyst, optionally free organophosphorus ligand, one or more first nonpolar solvents and one or more second nonpolar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products, said one or more first nonpolar solvents and said one or more second nonpolar solvents; (2) supplying said reaction product fluid from said reaction zone to a separation zone, (3) mixing said reaction product fluid in said separation zone to obtain by phase separation a nonpolar phase comprising said one or more unreacted reactants, said metal-organophosphorus ligand complex catalyst, said optionally free organophosphorus ligand, said one or more first nonpolar solvents and said one or more second nonpolar solvents and a polar phase comprising said one or more organophosphorus ligand degradation products, said one or more reaction byproducts and said one or more products, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (5) supplying from said separation zone to said reaction zone and/or said separation zone one or more recycle streams comprising said one or more unreacted reactants, said metal-organophosphorus ligand complex catalyst, said optionally free organophosphorus ligand, said one or more first nonpolar solvents and said one or more second nonpolar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

8. A continuous process for producing one or more products comprising: (1) reacting in a reaction zone one or more reactants in the presence of a metal-organophosphorus ligand complex catalyst, optionally free organophosphorus ligand and one or more first nonpolar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products and said one ormore first nonpolar solvents; (2) supplying said reaction product fluid from said reaction zone to a separation zone, (3) mixing said reaction product fluid in said separation zone with one or more second nonpolar solvents to obtain by phase separation a nonpolar phase comprising said one or more unreacted reactants, said metal-organophosphorus ligand complex catalyst, said optionally free organophosphorus ligand, said one or more first nonpolar solvents and said one or more second nonpolar solvents and a polar phase comprising said one or more organophosphorus ligand degradation products, said one or more reaction byproducts and said one or more products, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (5) supplying from said separation zone to said reaction zone and/or said separation zone one or more recycle streams comprising said one or more unreacted reactants, said metal-organophosphorus ligand complex catalyst, said optionally free organophosphorus ligand, said one or more first nonpolar solvents and said one or more second nonpolar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

9. A process for separating one or more organophosphorus ligand degradation products, one or more reaction byproducts and one or more products from a continuously generated reaction product fluid comprising one or more unreacted reactants, a metal-organophosphorus ligand complex catalyst, optionally free organophosphorus ligand, said one or more organophosphorus ligand degradation products, said one or more reaction byproducts, said one or more products and one or more nonpolar solvents, wherein said process comprises (1) supplying said reaction product fluid from a reaction zone to a separation zone, (2) mixing said reaction product fluid in said separation zone to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts and said one or more products, (3) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (4) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

10. A continuous process for producing one or more products comprising: (1) reacting in a reaction zone one or more reactants in the presence of a metal-organophosphorus ligand complex catalyst, optionally free organophosphorus ligand and one or more nonpolar solvents to form a reaction product fluid comprising one or more unreacted reactants, said metal-organophosphorus ligand complex catalyst, said optionally free organophosphorus ligand, one or more organophosphorus ligand degradation products, one or more reaction byproducts, said one or more products and said one or more nonpolar solvents; (2) supplying said reaction product fluid from said reaction zone to a separation zone, (3) mixing said reaction product fluid in said separation zone to obtain by phase separation a nonpolar phase comprising said one or more unreacted reactants, said metal-organophosphorus ligand complex catalyst, said optionally free organophosphorus ligand and said one or more nonpolar solvents and a polar phase comprising said one or more organophosphorus ligand degradation products, said one or more reaction byproducts and said one or more products, (4) removing from said separation zone an amount of said one or more organophosphorus ligand degradation products, said one or more reaction byproducts and said one or more products essentially equal to their rate of formation in said reaction product fluid in said reaction zone whereby the amount of said one or more organophosphorus ligand degradation products, said one or more reaction byproducts and said one or more products in said reaction product fluid in said reaction zone is maintained at a predetermined level, and (5) supplying from said separation zone to said reaction zone and/or said separation zone one or more recycle streams comprising said one or more unreacted reactants, said metal-organophosphorus ligand complex catalyst, said optionally free organophosphorus ligand and said one or more nonpolar solvents; wherein (i) the selectivity of the nonpolar phase for the organophosphorus ligand with respect to the one or more products is expressed by the partition coefficient ratio Ef1 defined in claim 1 which is a value greater than about 2.5, (ii) the selectivity of the nonpolar phase for the organophosphorus ligand with respect to the one or more organophosphorus ligand degradation products is expressed by the partition coefficient ratio Ef2 defined in claim 1 which is a value greater than about 2.5, and (iii) the selectivity of the nonpolar phase for the organophosphorus ligand with respect to the one or more reaction byproducts is expressed by the partition coefficient ratio Ef3 defined in claim 1 which is a value greater than about 2.5.

11. The process of claim 1 wherein Ef1 is a value of greater than about 3.0, Ef2 is a value of greater than about 3.0, and Ef3 is a value of greater than about 3.0.

12. The process of claim 3 which comprises a hydroformylation, hydroacylation (intramolecular and intermolecular), hydrocyanation, hydroamidation, hydroesterification, aminolysis, alcoholysis, hydrocarbonylation, reductive hydroformylation, hydrogenation, olefin oligomerization, hydroxycarbonylation, carbonylation, isomerization or transfer hydrogenation process.

13. The process of claim 1 wherein said one or more nonpolar solvents are selected from alkanes, alkadienes, cycloalkanes, alkenes, aldehydes, ketones, ethers, esters, amines, aromatics, silanes, silicones, carbon dioxide, and mixtures thereof.

14. The process of claim 1 wherein said one or more polar solvents are selected from nitriles, lactones, alkanols, cyclic acetals, water, pyrrolidones, formamides, sulfoxides, and mixtures thereof.

15. The process of claim 13 wherein said one or more nonpolar solvents are selected from propane, 2,2-dimethylpropane, butane, 2,2-dimethylbutane, pentane, isopropyl ether, hexane, triethylamine, heptane, octane, nonane, decane, isobutyl isobutyrate, tributylamine, undecane, 2,2,4-trimethylpentyl acetate, isobutyl heptyl ketone, diisobutyl ketone, cyclopentane, cyclohexane, isobutylbenzene, n-nonylbenzene, n-octylbenzene, n-butylbenzene, p-xylene, ethylbenzene, 1,3,5-trimethylbenzene, m-xylene, toluene, o-xylene, decene, dodecene, tetradecene, butadiene, heptadecanal, and mixtures thereof.

16. The process of claim 14 wherein said one or more polar solvents are selected from propionitrile, 1,3-dioxolane, 3-methoxypropionitrile, 1-methyl-2-pyrrolidinone, N,N-dimethylformamide, 2-methyl-2-oxazoline, adiponitrile, acetonitrile, epsilon caprolactone, water, glutaronitrile, 3-methyl-2-oxazolidinone, dimethyl sulfoxide, sulfolane, and mixtures thereof.

17. The process of claim 1 wherein said metal-organophosphorus ligand complex catalyst comprises rhodium complexed with an organophosphorus ligand represented by the formula:

(i) a triorganophosphine ligand represented by the formula:

wherein $R^1$ is the same or different and represents a substituted or unsubstituted monovalent hydrocarbon radical containing from 1 to 24 carbon atoms or greater;

(ii) a monoorganophosphite represented by the formula:

wherein $R^3$ represents a substituted or unsubstituted trivalent hydrocarbon radical containing from 4 to 40 carbon atoms or greater;

(iii) a diorganophosphite represented by the formula:

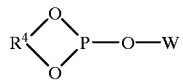

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

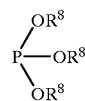

wherein each $R^8$ is the same or different and represents a substituted or unsubstituted monovalent hydrocarbon radical; and (v) an organopolyphosphite containing two or more tertiary (trivalent) phosphorus atoms represented by the formula:

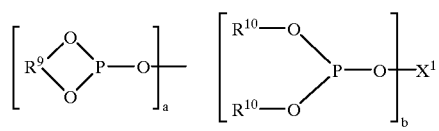

wherein $X^1$ represents a substituted or unsubstituted n-valent hydrocarbon bridging radical containing from 2 to 40 carbon atoms, each $R^9$ is the same or different and represents a divalent hydrocarbon radical containing from 4 to 40 carbon atoms, each $R^{10}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

18. The process of claim 3 wherein said separation zone comprises one or more vaporizers, one or more distillation columns, one or more fractional countercurrent extractors, or permissible combinations thereof in parallel or in series.

19. The process of claim 18 wherein said reaction product fluid first passes through a vaporizer or distillation column to remove at least some products, reaction byproducts and/or unreacted reactants and the resulting reaction product fluid, depleted in products, reaction byproducts and/or unreacted reactants, then passes to a fractional countercurrent extractor.

20. The process of claim 18 wherein said reaction product fluid first passes through a vaporizer or distillation column to remove at least some reaction byproducts and/or unreacted reactants and the resulting reaction product fluid, depleted in reaction byproducts and/or unreacted reactants, then passes to a fractional countercurrent extractor.

21. A reaction mixture comprising one or more products in which said reaction mixture is prepared by the process of claim 3.

22. The process of claim 3 further comprising derivatizing the one or more products.

23. The process of claim 22 in which the derivatizing reaction comprises hydrogenation, esterification, etherification, amination, alkylation, dehydrogenation, reduction, acylation, condensation, carboxylation, carbonylation, oxidation, cyclization, reductive amination, silylation, hydrolysis, polymerization, copolymerization and permissible combinations thereof.

* * * * *